US006946002B2

(12) United States Patent
Geitz

(10) Patent No.: US 6,946,002 B2
(45) Date of Patent: Sep. 20, 2005

(54) INTRAGASTRIC STENT FOR DUODENUM BYPASS

(75) Inventor: Kurt Geitz, Sudbury, MA (US)

(73) Assignee: Boston Scientific Corporation, Natick, MA (US)

( * ) Notice: Subject to any disclaimer, the term of this patent is extended or adjusted under 35 U.S.C. 154(b) by 0 days.

(21) Appl. No.: 10/839,317

(22) Filed: May 5, 2004

(65) Prior Publication Data

US 2004/0204768 A1 Oct. 14, 2004

Related U.S. Application Data

(63) Continuation of application No. 10/057,434, filed on Jan. 25, 2002, now Pat. No. 6,740,121, which is a continuation of application No. 10/007,889, filed on Nov. 9, 2001, now abandoned.

(51) Int. Cl.[7] .................................................. A61F 2/04
(52) U.S. Cl. ................. 623/23.7; 623/23.65; 623/23.75
(58) Field of Search ............................. 623/1.13, 23.64, 623/23.65, 23.67, 23.71, 23.7, 23.75

(56) References Cited

U.S. PATENT DOCUMENTS

| 4,315,509 | A | 2/1982 | Smit |
| 4,648,383 | A | 3/1987 | Angelchik |
| 5,306,300 | A | 4/1994 | Berry |
| 2002/0161341 | A1 | 10/2002 | Stinson et al. |
| 2003/0040804 | A1 | 2/2003 | Stack et al. |

OTHER PUBLICATIONS

Benjamin, S.B., et al., "Double–Blind Controlled Trial of the Garren–Edwards Gastric Bubble: An Adjunctive Treatment for Exogenous Obesity," *Gastroenterology* 95(3):581–588, Sep. 1988.

Coelho, J.C.U., and Campos, A.C.L., "Surgical Treatment of Morbid Obesity," *Current Opinion in Clinical Nutrition and Metabolic Care* 4(3):201–206, May 2001.

Hubert, H.B., et al., "Obesity as an Independent Risk Factor for Cardiovascular Disease: A 26–year Follow–up of Participants in the Framingham Heart Study," *Circulation* 67(5):968–977, May 1983.

Kral, J.G., "Gastric Ballons: A Plea for Sanity in the Midst of Balloonacy" *Gastroenterology* 95(1):213–215, Jul. 1988.

Kral, J.G., "Overview of Surgical Techniques for Treating Obesity," *American Journal of Clinical Nutrition* 55(2):552S–555S, 1992.

Macgregor, A.MC., and Rand, C.S.W., "Gastric Surgery in Morbid Obesity," *Archives of Surgery* 128(10):1153–1157, Oct. 1993.

MacLean, L.D., et al., "Results of the Surgical Treatment of Obesity," *The American Journal of Surgery* 165:155–162, Jan. 1993

Mathus–Vliegen, E.M.H., et al., "Intragastric Balloon in the Treatment of Super–morbid Obesity," *Gastroenterology* 99(2):362–369, Aug. 1990.

Meshkinpour, H., et al., "Effect of Gastric Bubble as Weight Reduction Device: A Controlled, Crossover Study," *Gastroenterology* 95(3):589–592, Sep. 1988.

Mun, E.C., et al., "Current Status of Medical and Surgical Therapy for Obesity," *Gastroenterology* 120(3):669–681, Feb. 2001.

Pi–Sunyer, F.X., "Medical Hazards of Obesity," *Annals of Internal Medicine* 119(7):655–660, Oct. 1993.

*Primary Examiner*—Corrine McDermott
*Assistant Examiner*—William H Matthews
(74) *Attorney, Agent, or Firm*—Christensen O'Connor Johnson Kindness PLLC

(57) ABSTRACT

A porous weave of bioabsorbable filaments is encased in an elastic membrane to form a thin-walled stent. The stent is sized to be snugly fitted in the proximate portion of the duodenum of a patient, to induce weight loss by limiting uptake of food passing through the stent. After a predetermined period, the stent degrades and passes from the body without surgical intervention.

5 Claims, 1 Drawing Sheet

(12)	INTRAGASTRIC STENT FOR DUODENUM BYPASS

This application is a continuation of U.S. patent application Ser. No. 10/057,434, filed Jan. 25, 2002, now U.S. Pat. No. 6,740,121, which was a continuation of U.S. patent application Ser. No. 10/007,889, filed Nov. 9, 2001, now abandoned.

FIELD OF THE INVENTION

The present invention relates to an impervious, resilient, flexible, biocompatible stent that can be secured in the duodenum adjacent to the pylorus to effect weight loss over a controlled period.

BACKGROUND OF THE INVENTION

The incidence of obesity and its associated health-related problems have reached epidemic proportions in the United States. See, for example, P. C. Mun et al., "Current Status of Medical and Surgical Therapy for Obesity" *Gastroenterology* 120:669–681 (2001). Recent investigations suggest that the causes of obesity involve a complex interplay of genetic, environmental, psycho-behavioral, endocrine, metabolic, cultural, and socioeconomic factors. Severe obesity is frequently associated with significant comorbid medical conditions, including coronary artery disease, hypertension, type II diabetes mellitus, gallstones, nonalcoholic steatohepatitis, pulmonary hypertension, and sleep apnea.

Estimates of the incidence of morbid obesity are approximately 2% of the U.S. population and 0.5% worldwide. Current treatments range from diet, exercise, behavioral modification, and pharmacotherapy to various types of surgery, with varying risks and efficacy. In general, nonsurgical modalities, although less invasive, achieve only relatively short-term and limited weight loss in most patients. Surgical treatments include gastroplasty to restrict the capacity of the stomach to hold large amounts of food, such as by stapling or "gastric banding." Other surgical procedures include gastric bypass and gastric "balloons" which, when deflated, may be inserted into the stomach and then are distended by filling with saline solution.

The need exists for cost effective, less invasive interventions for the treatment of morbid obesity.

SUMMARY OF THE INVENTION

The present invention provides a novel system for treatment of morbid obesity by use of a bioabsorbable stent fitted snugly in the duodenum adjacent to the pylorus and impervious to digestive juices to limit the uptake of food passing through the stent. The stent is thin-walled, elastic, and flexible so as not to interfere with normal shifting of the duodenum nor with the passage of food therethrough. The stent can be formed of bioabsorbable material such that after a predetermined period the stent degrades and passes out of the body without the necessity for additional surgical intervention.

In the preferred embodiment, the stent includes a weave of bioabsorbable filaments and a covering or coating of impervious material or membrane. Alternatively, the weave can be integrated within the membrane. The filaments preferably have memory characteristics tending to exert moderate pressure against the interior wall of the duodenum, and the stent can possess regional variable strength, structure and bioabsorption pharmacokinetics. The stent can be secured in place by sutures at its proximate and distal ends.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention provides an elastic, flexible, impervious stent adapted to be secured within a patient's duodenum to limit uptake of food in that area and thereby assist in weight loss.

Figure 1:
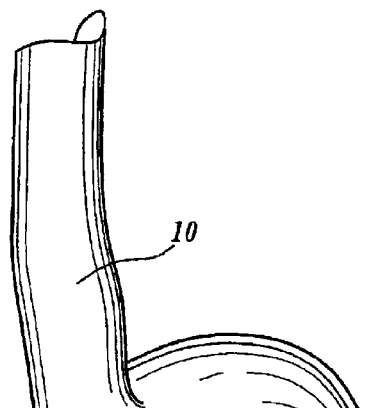
FIG. 1 is a somewhat diagrammatic elevation of a stomach and adjacent parts of the alimentary canal, with the wall of the distal pyloric part and duodenum broken away to reveal an intragastric stent in accordance with the present invention.

FIG. 1 illustrates a central portion of the alimentary canal, including the distal segment of the esophagus 10, the stomach 12, and the duodenum 14 (proximate segment of the small intestine). The pyloric part 16 of the stomach leads to the duodenum 14 by way of the gastric outlet or pylorus 18. The pylorus forms the distal aperture of the stomach and has an enclosing circular layer of muscle which is normally contracted to close the aperture but which relaxes to provide an open but restricted passage. Although subject to substantial variation in different individuals, in a representative patient the pylorus has a maximum open diameter of about 2 cm, and the duodenum has a diameter which typically is about 18–20 mm in diameter.

In accordance with the present invention, a flexible, thin-walled stent 20 fits snugly in the duodenum from a location adjacent to the pylorus 18 to a location substantially distally therefrom, approximately 6 cm to approximately 12 cm in a preferred embodiment. The stent can be inserted through the esophagus and have its proximate and distal ends secured by endoscopic suturing, which is a minimally invasive procedure as compared to other surgical interventions used for treating morbid obesity.

Figure 2:
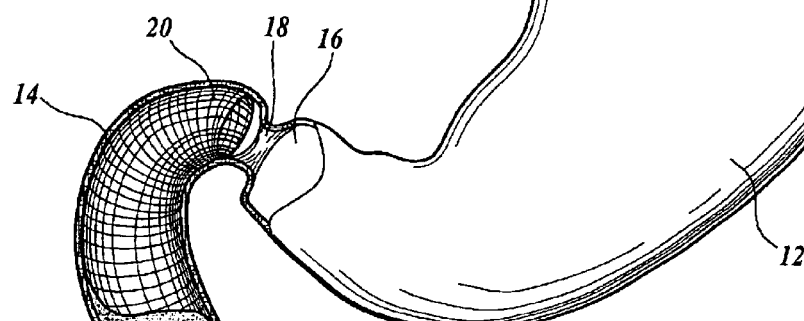
FIG. 2 is a side elevation of the stent of FIG. 1 prior to insertion in the duodenum.
Figure 2:
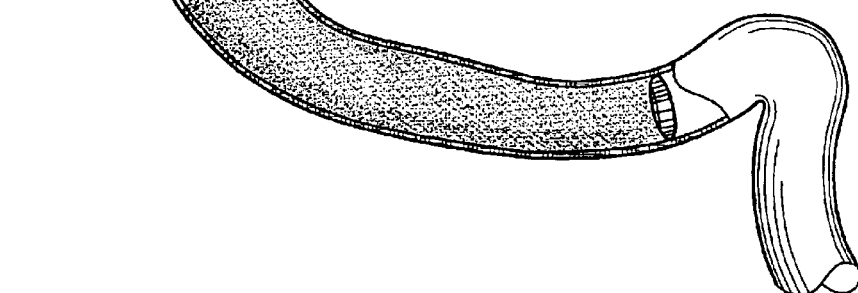
Figure 2:
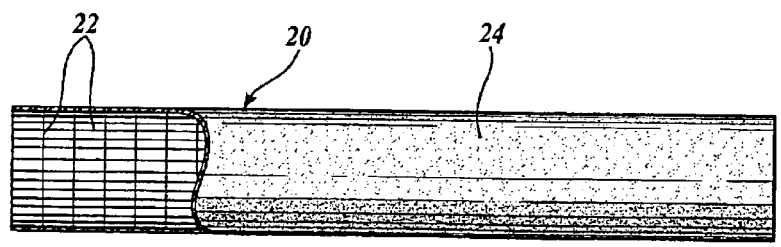

With reference to FIG. 2, preferably the stent 20 is formed as a thin-walled cylinder including woven filaments 22. The filaments form a woven shell having the desired memory characteristics that maintain the generally cylindrical shape and the resiliency that allows the stent to be compressed and bulged at different locations along its length. In addition, the filaments are formed of bioabsorbable material, such as polyglycolic acid polymer or polylactic acid polymer. The primary function of the fibrous weave is to obtain the desired shape-retaining characteristics, but such a weave will typically be porous, or at least porous enough that digestive juices would pass therethrough and partially or totally defeat the purpose of the stent in preventing uptake of food through the duodenum. Consequently, the woven filaments are encased in an impervious elastic membrane 24 or incorporated within such a membrane. The membrane also provides a smooth exterior for the stent, lessening the chance of irritation of the lining of the duodenum.

Various manners of manufacture of the stent are possible. The woven filament part may be formed first and inserted through a cylindrical elastic membrane. Another possibility is to insert the fibrous cylinder onto a mandrel and spray or dip the mandrel in a settable liquid which solidifies to form the coating. The woven part of the stent also can be spun of fine filaments on a mandrel which thereafter is sprayed with such a settable liquid, with or without a chopped fiber reinforcing material.

It is preferred for the present invention that the entire stent, including woven filaments and membrane, be bioabsorbable over a period of time estimated to result in a desired weight loss. Such period could be from three months to two years, preferably about six months. At the end of the selected period, the stent degrades and passes from the body without intervention. Due to the noninvasive nature of placement and passing of the stent, the procedure can be repeated if necessary in order to achieve the desired weight loss.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An intragastric stent comprising a substantially cylindrical thin-walled shell sized for snug fitting in a duodenum adjacent to the pylorus without extending into the stomach, the shell including an elastic membrane impervious to digestive juices such that, when deployed in the duodenum, uptake of food through the stent is lessened or inhibited, the shell being bioabsorbable so that the shell will pass from the duodenum without surgical intervention after an approximately predetermined period of 3 months to 2 years.

2. The stent defined in claim 1, in which the approximately predetermined period is about 6 months.

3. The stent defined in claim 1, in which the shell has a length of about 6 cm to about 12 cm.

4. A method of inducing weight loss in a patient which comprises securing in the proximate portion of the duodenum of the patient, adjacent to the pylorus without extending into the stomach, a substantially cylindrical, thin-walled, flexible elastic stent which, when deployed, is impervious to digestive juices in the duodenum to limit uptake of food through the stent and along the portion of the duodenum in which the stent is fitted, the stent including an elastic membrane, the membrane being bioabsorbable so that the stent will pass from the duodenum within an approximately predetermined period of 3 months to 2 years.

5. The method described in claim 4, in which the approximately predetermined period is 6 months.

* * * * *

UNITED STATES PATENT AND TRADEMARK OFFICE
CERTIFICATE OF CORRECTION

PATENT NO. : 6,946,002 B2 Page 1 of 1
DATED : September 20, 2005
INVENTOR(S) : K. Geitz It is certified that error appears in the above-identified patent and that said Letters Patent is hereby corrected as shown below:

Title page,
Item [*] Notice, insert -- This patent is subject to a terminal disclaimer. --.

Signed and Sealed this

Fourteenth Day of March, 2006

JON W. DUDAS
*Director of the United States Patent and Trademark Office*